United States Patent [19]

Faccioli et al.

[11] Patent Number: 5,320,622
[45] Date of Patent: Jun. 14, 1994

[54] DYNAMIC AXIAL SPLINT

[75] Inventors: Giovanni Faccioli, Monzambano; Daniele Venturini, Verona, both of Italy

[73] Assignee: Orthofix S.r.l., Bussolengo, Italy

[21] Appl. No.: 55,854

[22] Filed: Apr. 30, 1993

[30] Foreign Application Priority Data

Jul. 28, 1992 [IT] Italy .......................... VR92A000070

[51] Int. Cl.⁵ .......................... A61B 17/60; A61F 5/04
[52] U.S. Cl. ........................................ 606/58; 606/59
[58] Field of Search ...................... 606/53–59

[56] References Cited

U.S. PATENT DOCUMENTS 2,333,033 10/1943 Mraz ...................................... 606/59
5,026,372 6/1991 Sturtzkopf et al. ................... 606/59

Primary Examiner—Tamara L. Graysay
Attorney, Agent, or Firm—Hopgood, Calimafde, Kalil & Judlowe

[57] ABSTRACT

A dynamic external axial splint for use in rehabilitating a fractured bone comprises a pair of spaced clamps for bone screws or bolts anchored to the respective fragments of the fractured bone. A central body releasably and universally connects and locks these spaced clamps via ball-joints having provision for selective retention of a wide variety of angular relations, between the central body and the central axis of each of the spaced clamps. The central body comprises first and second end members and a third or intermediate member, affording on the one hand, longitudinally and adjustably fixed lap of one end member with the intermediate member, and also affording limited resiliently snubbed and axially guided displaceability as between the intermediate member and the other end member, thus rendering the two end members and the respective bone-fragment anchorages clamped to the end members subject to the same axially guided and resiliently snubbed action. The axially displaceable and resilient snubbed action is selectively neutralized by a single clamp adjustment which converts the dynamic external splint into a fixed external splint or fixator.

22 Claims, 3 Drawing Sheets

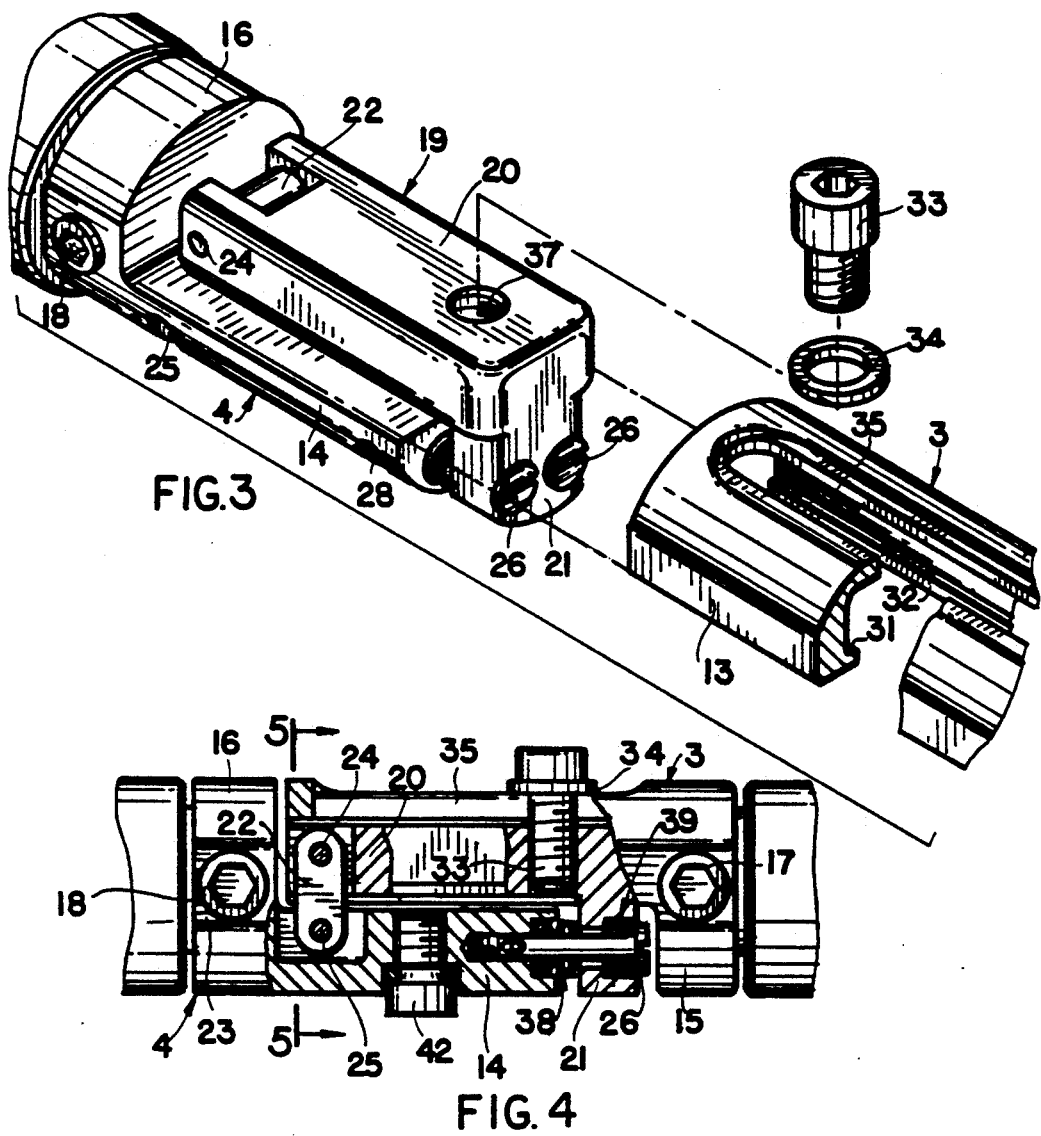
FIG.3
FIG.4
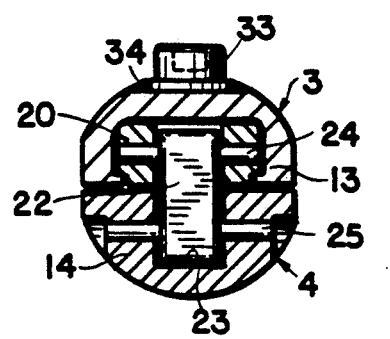
FIG.5

DYNAMIC AXIAL SPLINT

BACKGROUND OF THE INVENTION

This invention relates to an external axial splint, or fixator, in particular for the dynamic repair of bone fractures.

For many years, it has become a practice in bone surgery to employ an external fixation device, essentially comprising a substantially rigid structure provided with bone-anchoring screws or bolts that are inserted in bone fragments on opposite sides of a given fracture, to encourage knitting of the bone by stabilizing the relative position of the involved bone fragments.

It has been noted that, with some types of fracture, knitting times can be accelerated and ultimate stability can be increased by exerting axial compression upon the bone fragments.

In the use of rigid external splints (fixators), muscular forces and/or external stresses are in general transmitted to the splint and not to the fractured bone. But, to encourage regeneration of hard bone, it is preferred that the patient apply some stress to the bone, to encourage more rapid and reliable knitting at the situs of the fracture. Conventional systems do not permit the application of such forces to the bone, on account of their relative rigidity and lack of deformability.

To overcome the problem of relative rigidity, U.S. Pat. No. 5,026,372 discloses a dynamic axial splint wherein an articulated parallelogram joint is the means of yieldably interconnecting spaced clamps that are respectively anchored to the separate fragments of a fractured bone. Specifically, the parallelogram joint comprises two spaced longitudinal members pivotally connected at their ends by two pairs of transverse links, thus allowing limited longitudinal displacement of one with respect to the other of the longitudinal members, when the joint is subjected to a compression force or a tension force.

A disadvantage of this known axial splint lies in the fact that, when the opposing members are subject to longitudinal displacement, they are also caused to move to some extent in a transverse direction, as governed by the accompanying angular displacement of the connecting links. Thus, the clamps which anchor the respective fragments of fractured bone lose their longitudinal alignment and have an adverse effect on the point of fracture. It has in fact been established that bony material which is undergoing consolidation has a very much lesser resistance to transverse (shear) forces than to bending or longitudinal forces. Thus, to contain the transverse movement, provision is made to limit relative longitudinal displacement of the longitudinal members to a few millimeters, but the indicated disadvantage is already appreciable with longitudinal displacements of a few tenths of a millimeter.

A further disadvantage of this known dynamic splint lies in the fact that, in order to repair or correct the fracture while the bony material is undergoing consolidation, the means for arresting dynamic movement must be released because of the particular configuration of the parallelogram joint and the manner in which it is anchored to opposing members fitted with clamps.

Another disadvantage of this known axial splint lies in its appreciable complexity and excessive cost due to the existence within the articulated parallelogram of a number of joints which among other things increase the risk of jamming at pivot connections.

BRIEF STATEMENT OF THE INVENTION

A primary object of the invention is to eliminate or at least substantially reduce the above-mentioned disadvantages by providing an external axial splint which is particularly suited for the dynamic repair of bone fractures and which maintains central-body members fixed to the respective fragments of a fractured bone in a substantially longitudinal alignment throughout a range of dynamic axial displacement.

Another object of the invention is to provide an external axial splint having high axial mobility within a strictly controlled range of movement so as to reduce to a minimum any risk of jamming during application to the patient.

It is also an object to provide an axial split which can induce beneficial non-harmful movements in the bone fragments in order to regenerate hard bone.

A further object is to provide a dynamic axial splint in which the dynamic function and repair of the fracture are absolutely independent and can be selectively controlled.

Yet another object of the invention is to provide an external axial splint of relatively simple structure and with a reduced number of component parts.

These objects, together with others which will become more apparent below, are accomplished through an external axial splint, especially for the dynamic repair of bone fractures, comprising a pair of spaced clamps for bone screws or bolts anchored to the respective fragments of a fractured bone, a central body formed of a pair of end members or heads each of which can be coupled to one of the clamps via a ball joint, and securing means for selectively immobilizing each ball joint in a predetermined angular position; the central body comprises an intermediate member which connects the end members via longitudinal guide means that is strictly longitudinal, the guided connection of the intermediate member to one of the end members being adjustably fixed, while the guided connection of the intermediate member to the other end establishes limited resiliently snubbed axial displaceability of the end members with respect to each other. A loose-link connection between the intermediate member and the other end member provides assurance that the resiliently snubbed axial-displaceability feature cannot be jammed or otherwise impaired.

The primary advantage of the present invention is that the strictly longitudinal nature of the guide means inherently avoids the transverse movement of end members which normally occur in known axial splints having parallelogram-joint action. Excellent axial mobility is assured, without jamming or other misaligning impairment.

Finally, the splint of the invention is structurally simple, light and reliable, and a degree of selectively variable axially compliant action is afforded, with clear economic and functional advantages.

DETAILED DESCRIPTION

A preferred embodiment of the invention will be described in detail, in connection with the accompanying drawings, in which:

FIG. 3 is an enlarged and exploded view of certain parts of the splint of FIGS. 1 and 2;

FIG. 4 is a view in side elevation, partly broken away and generally in longitudinal section, for the central body portion of the splint of FIGS. 1 and 2;

FIG. 5 is a transverse section taken at 5—5 in FIG. 4;

Figure 1:
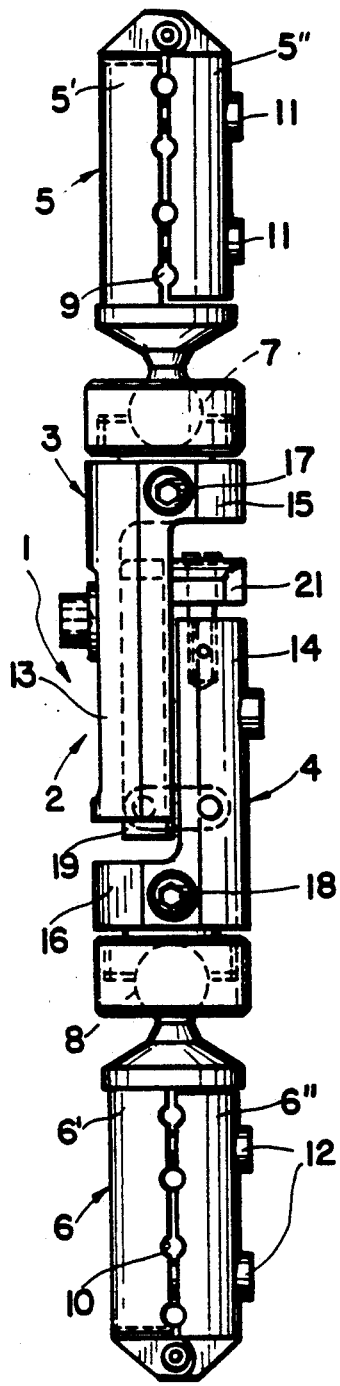
FIG. 1 is a view in side elevation of a dynamic axial splint of the invention, complete with bone-screw clamps at the respective ends of the splint.
Figure 2:
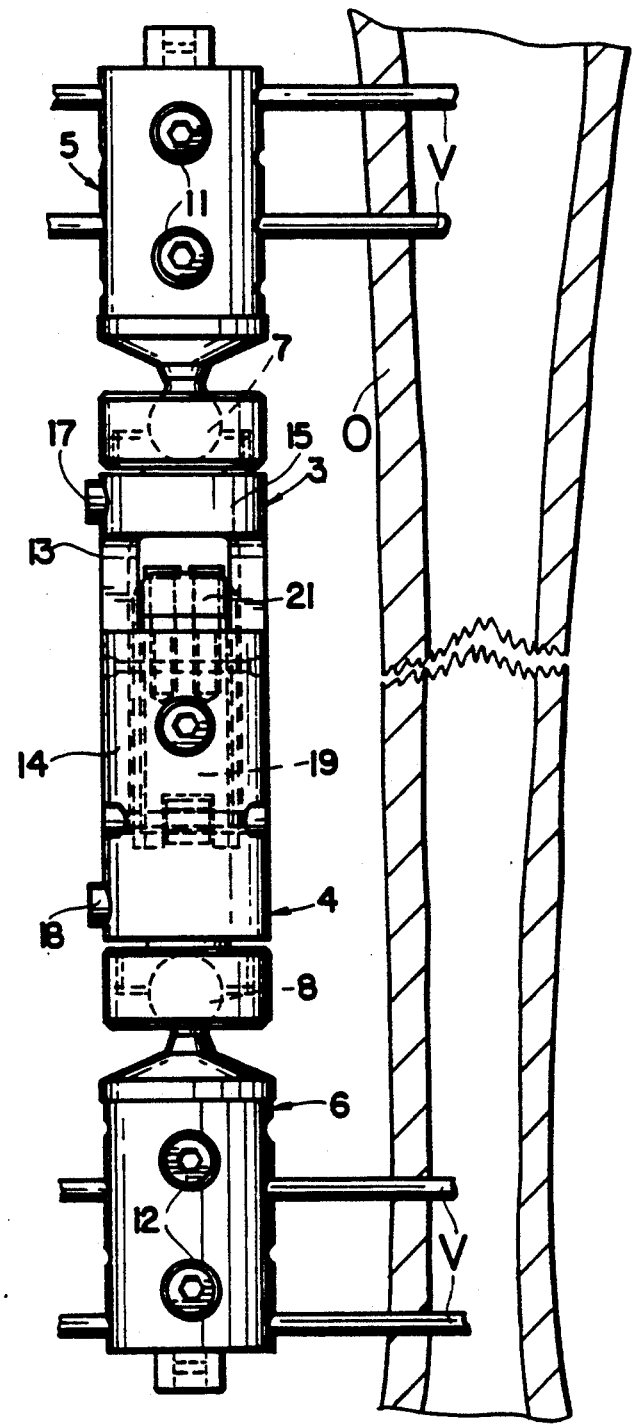
FIG. 2 is another view in side elevation of the splint of FIG. 1 but taken from an aspect that is 90 degrees offset from the aspect of FIG. 1, the bone-screw clamps being shown in FIG. 2 to be anchored to the respective fragments of a fractured bone.

In FIGS. 1 and 2, a dynamic external axial splint of the invention is generally indicated by reference numeral 1 and is seen to comprise a central body 2 having two end members 3, 4 each of which is coupled to an associated clamp 5, 6, via ball-joints 7, 8.

Each clamp 5, 6 may be of generally ellipsoidal section, constructed of two opposing halves 5', 5" and 6', 6" respectively, and having transversely grooved seats 9, 10 and bolts 11, 12 for securely clamping bolts or screws V which will be understood to have been anchored in the cortical tissue of a fractured bone O. As shown, the outer ends of the halves of each clamp are hinge-connected to each other, and one half (5', 6') of each clamp is fixedly related to the ball (7,8) of its associated ball-joint connection to the central body 2.

The body members 3, 4 are the first and second of three parts constituting the central body 2. Each of these first two parts 3,4 has an elongate portion 13 (14) of generally semi-cylindrical section and is integrally formed at one end with a generally cylindrical head 15 (16). The semicylindrical portions 13, 14 are longitudinally lapped, such that the overall appearance of central body 2 is in generally cylindrical conformance with the two heads 15 (16), adjacent to socket components of the respective ball joints 7 (8). Transverse bolts 17 (18) through the heads 15 (16) will be understood to enable releasable clamping of the respective ball joints 7 (8) for selective setting of particular angular orientation of the longitudinal axis of each bone screw clamp 5 (6) with respect to the longitudinal axis of central body 2, namely, with respect to the axis determined by the geometric line between ball centers at 7, 8. The overall generally cylindrical appearance of the central body applies for the entire range of adjustable overlap of the elongate semi-cylindrical portions 13 (14), as will later become clear.

The third part of the central body is an elongate intermediate member 19 having means determining the longitudinal connection between parts 3, 4 and any relative longitudinal displacement of parts 3, 4 with respect to each other, while also preventing any relative rotation of parts 3, 4 about the axis of the central body, or any significant axial misalignment of either of parts 3, 4 with respect to the axis of the central body.

As best seen in FIG. 3, the elongate intermediate member 19 extends at 20 with constant generally rectangular section for lap of substantially the longitudinal extent of the generally semicylindrical portion 14. At the remote end of member 19, i.e., remote from head 16 of the body part 4 which it substantially laps, member 19 is integrally formed with a transverse head 21.

Figure 6:
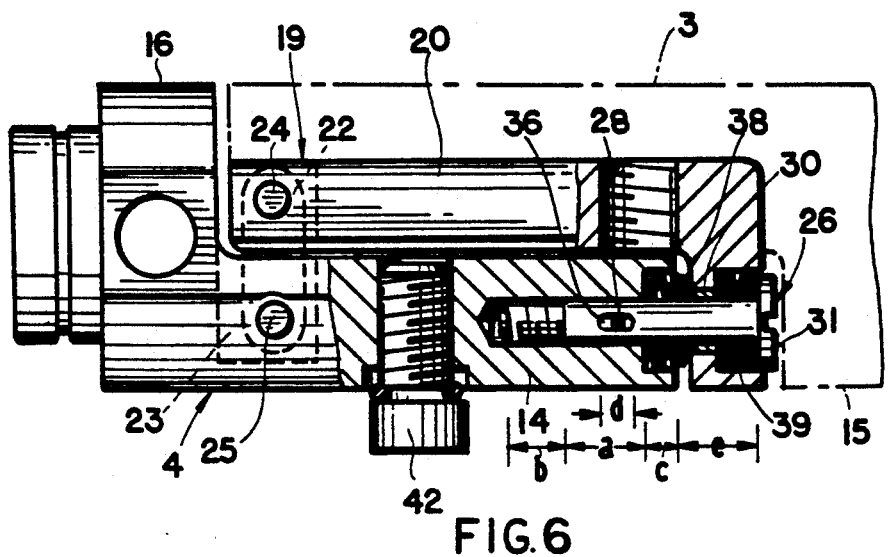
FIG. 6 is a further enlarged view in side elevation, partly broken away and generally in longitudinal section, to more clearly show the coaction between axially displaceable parts of the central body portion of the split.

The intermediate member 19 has a resiliently snubbed and longitudinally guided relation to body part 4, wherein longitudinal guidance derives from the cylindrical shanks of two spaced parallel bolts 26 having relatively deep threaded engagement to tapped threads near the inner ends of deep longitudinal bores in the remote end of the generally semicylindrical portion 14 of body part 4. In FIG. 6, longitudinal dimensional notations are helpful in a description of one of the bolts 26 and the bore to which it is fitted, it being understood that both bolts are identical. The dimensional notations a, b, c reflect the full effective depth of the bore, wherein the deeply threaded portion is of limited extent b, and wherein, except for the shallow depth c of a counterbore, a major fraction a of the bore is cylindrical, for accurate and substantial determination of correct orientation and support of the cylindrical remainder of the shank of the bolt 26, such that the cylindrical shank portion also projects beyond body portion 14, and through an aligned bore and counterbore in the transverse head portion 21 of intermediate body member 19. A precision-fitted bushing 30 in each of the bores of head 21 is of hardened material and TEFLON-lined*, for low-friction guidance on the bolt shank. The bolt shank terminates at an enlarged head 31 having an exposed transverse slot for screwdriver adjustment. First and second sets of dished spring washers 38, 39, sometimes known as Belleville springs, are located in the respective counterbores in body portions 14 and 21, and the threaded advance of each of the bolts will be understood to selectively determine an axially preloaded and longitudinally neutral position of the intermediate body member 19 with respect to body member 4. A transverse slot 36 in each bolt shank will register with a single transverse pin alignment 28 through both bores in body portion 14, twice for each adjusted full turn of bolts 26, and for a range d of several consecutive turns of bolt adjustment, thus enabling pin 28 to lock a given selected spring preload of the neutral position of body members 4, 19, with respect to each other.

* Teflon is a DuPont Company trademark for its tetrafluoroethylene products.

At its other end, namely, the end adjacent head 16, the intermediate member may be retained against such transverse displacement as might otherwise jeopardize the fidelity of purely axial displaceability of intermediate member 19 with respect to body member 4. This may be assured by a rod-and-bore engagement similar to what has been described for bolts 26 and their bore-guiding function, but in the form shown it is indicated that a simple transverse link connection at 22 will serve the purpose, in view of the reality that the order of magnitude of maximum displaceability of members 14, 19 is 1.5 mm either side of the longitudinally neutral position. As shown, body part 4 is locally recessed at 23, and the corresponding end of intermediate member 19 is locally recessed to define transversely spaced arms for pivotal connection to the upper end of link 22 via a single pin 24; in similar fashion, another transverse pin 25 pivotally connects the lower end of link 22 to body part 4, between confronting sidewalls of the recess 23 in body part 4. A degree of looseness or play is tolerable in one or the other of the link (22) connections because the function of link 22 is primarily to assure against any jamming or frictional misalignment of the shank of bolt 26 with respect to its truly axial and resiliently snubbed guidance of the head bushing 30.

The connected relation of body part 3 to the intermediate member is one of selected longitudinal adjustment followed by clamping to retain the adjusted position. Specifically, for the longitudinal extent of maximum overlap of body part 3 with intermediate member 19, the interior of part 3 is recessed to define a generally rectangular shell which derives longitudinal guidance from the generally rectangular section of portion 20 of member 19, all as clearly seen in the cross-section of FIG. 5. This guided relation is totally secured by integrally formed longitudinal flanges 31, 32 of body part 3 engaging under bottom edges of portion 20 of intermediate member 19. A given fixed longitudinal adjustment of body part 3 to intermediate member 19 is achieved via a single bolt 33 and its washer 34, with bolt 33 passing through an elongate slot 35 in the portion 13 of part 3, and with bolt 33 tightly engaged to the threads of a tapped bore 37 in intermediate member 19, as seen in FIG. 4 for the most longitudinally compact adjustment of part 3 on member 19.

In the initial phase of applying the described dynamic axial splint to set the segments of a given fracture, it is desirable that the splint shall be a true fixator, i.e., with no provision for dynamic resiliently snubbed displacement of bone fragments. In such case, a set screw 42, frictionally retained by an elastomeric O-ring in a tapped transverse bore in portion 14 of body part 4 may be selectively driven against the underside of portion 20 of intermediate member 19, thereby completely rigidizing the spacing between bone-screw clamps 5, 6. Then later, as healing proceeds, release of set screw 42 from engagement with portion 20 will release the parts for dynamic-splint action.

Figure 7:
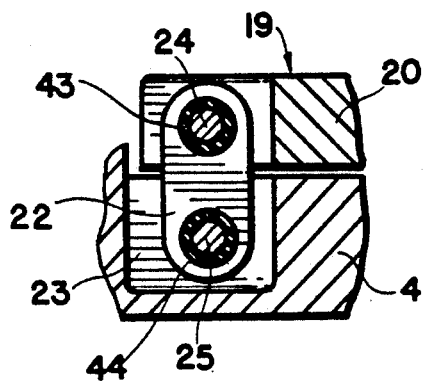
FIG. 7 is a fragmentary view in longitudinal section to show a modification.

The fragmentary diagram of FIG. 7 is a detailed showing of a slight modification wherein resiliently snubbed displacements of the described nature can be at least in part implemented via relatively stiff elastomeric bushings 43, 44 which serve the upper and lower pin connections 24, 25 of link 22, it being understood that bushings 43, 44 are bonded both to their respective pins 24, 25 and to their respective bores in link 22, as well as to the pin-mounting bores in portions 14 and 20 respectively, thereby making bushings 43, 44 contribute to the resilient snubbing action via transient torsional stressing of the two elastomeric bushings.

In use of the described dynamic axial splint, it is desirable to select and appropriately adjust the degree of resilient snubbing action, as in accordance with the orthopedic surgeon's evaluation of each patient's weight and potential for compressive strength in each fractured bone. The described embodiment in connection with FIG. 6 permits a degree of such adjustment, merely by removing the bolt-locking transverse pin 28, so that adjusted preload of both spring sets 38, 39 can be made via a limited number of half-turn screwdriver-adjusted displacements of bolts 26. Alternative, or further, adjustability can follow from selecting individual spring sets at 38, 39 for substituted assembly, in place of those shown in the drawings. For example, dished-washer stainless-steel springs and spring sets commercially available from Adolf Schnorr GmbH & Co. KG, of Sindelfingen, Federal Republic of Germany, offer a great variety of spring sizes and of spring constants, to suit the surgeon's prescription for the complete range of patient sizes and requirements.

The foregoing description of bolts 26 may be viewed as involving longitudinal guidance via a rod-and-bore engagement, for each of the bolts 26. The threaded deep-bore engagement, coupled with the cylindrical shank and its close-fitting support in the bore of portion 14, and over the relatively great axial span a establishes the projecting remainder of the cylindrical part of the shank as a precision reference for axial guidance of the bushed region 30 of the intermediate member 19. In the circumstances, it is appropriate to refer to this bushing 30 and cylindrical-shank engagement as a rod-and-bore engagement, which by reason of the opposed preloading of spring sets at 38, 39 establishes resiliently snubbed and longitudinally guided displaceability of the intermediate body part 19 with respect to one (4) of the central body parts. For the limited range of such guided displaceability, namely, in the order of 1.5 mm either side of the neutral or equilibrium position, angular displacement of link 22 involves insignificant axial misalignment of the longitudinal axes of the central body parts 3 and 4, particularly if link pins 24, 25 are in a geometric plane that is normal to the axis of body 2, for the equilibrium condition established by spring sets 38, 39. The insignificance of such axial misalignment flows from the fact that the bone-anchoring bolts or screws (V) respectively clamped to different fragments of the fractured bone (0) are themselves subject to small bending deflection when the fractured bone is under longitudinal stress, as when transiently weight-bearing or when a longitudinal adjustment of the spacing between clamps 5, 6 is intentionally made by the surgeon in the course of bone healing.

Figure 8:
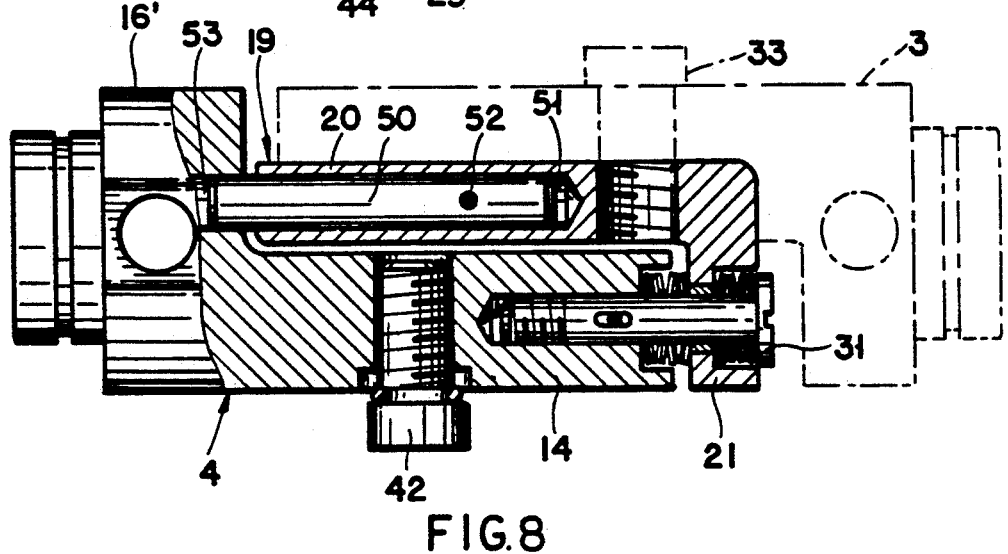
FIG. 8 is a view similar to FIG. 6, to show a further modification.

In the alternative construction shown in FIG. 8, the link 22 is replaced by another rod-and-bore engagement, involving coaction between a rod 50 that is fixed to intermediate member 19 and longitudinally oriented in a bore 51, being shown fixed by a transverse pin 52. Rod 50 projects for slidable engagement in an axially aligned bore 53 in the head 16 of body part 4. All other parts may be as described for FIG. 6, and therefore the same reference numbers are used, where applicable. In use, resilient snubbing of limited axially displaceability of body parts 3, 4 is available, under assured conditions of axial displaceability.

What is claimed is:

1. Orthopedic bone-fixator apparatus, for the dynamic repair of a bone fracture, comprising an elongate body having a longitudinal axis that is common to a head at each of the opposite ends of said body, said body comprising:

first and second body parts having longitudinally lapped portions each of which has an outer end which is integrally formed with one to the exclusion of the other of said heads;

each of said heads being adapted for selectively locked ball-joint connection of a bone-pin mount to each of the respective first and second body parts;

a third elongate body part carried by the lapped portion of said first body part;

first longitudinal guide means and a releasable clamp coacting between said second and third body parts for selectively determining a fixed longitudinal position of second body-part connection to said third body part; and second longitudinal guide means and resilient snubber means coacting between said first and third body parts for establishing limited resiliently snubbed and longitudinally guided displaceability of said third body part with respect to said first body part.

2. Apparatus according to claim 1, wherein said resilient snubber means is operative to resiliently snub longitudinally guided compressional displacement as well as to resiliently snub longitudinally guided tensed displacement of said third body part with respect to said first body part.

3. Apparatus according to claim 1, in which selectively operable clamp means coacting between said first and third body parts is operative to fix the first and third body parts and thus selectively to look said first and third body parts against longitudinally guided displaceability.

4. Apparatus according to claim 1, in which said second longitudinal guide means includes a first longitudinal rod-and-bore engagement coacting via one longitudinal end of said third body part, and a second longitudinal rod-and-bore engagement coacting via the opposite longitudinal end of said third body part.

5. Orthopedic bone-fixator apparatus, for the dynamic repair of a bone fracture, comprising an elongate body having a longitudinal axis that is common to a head at each of the opposite ends of said body, said body comprising:
first and second body parts having longitudinally lapped portions each of which has an outer end which is integrally formed with one to the exclusion of the other of said heads;
each of said heads being adapted for selectively locked ball-joint connection of a bone-pin mount to each of the respective first and second body parts;
a third elongate body part carried by the lapped portion of said first body part;
longitudinal guide means and a releasable clamp coacting between said second and third body parts for selectively determining a fixed longitudinal position of second body-part connection to said third body part; and
means including at least one longitudinal rod-and-bore engagement and resilient snubber means establishing limited resiliently snubbed and longitudinally guided displaceability of said third body part with respect to said first body part.

6. Apparatus according to claim 5, in which there are two longitudinal rod-and-bore engagements, on spaced parallel longitudinal axes.

7. Apparatus according to claim 6, in which said third body part integrally includes a transversely offset end portion that is in radial overlap with the end of said first body part remote from the headed end of said first body part, both of said spaced rod-and-bore engagements being via said transversely offset end portion.

8. Apparatus according to claim 7, in which each of said rod-and-bore engagements comprises aligned bores in said offset end portion and in said first body part; each of said rod-and-bore engagements further comprising a rod supported in and fixed to said fist body part and projecting through the bore of said offset end portion, said rod having a headed outer end, first spring means guided by said rod and poised for compressional reaction between said headed outer end and said offset end portion, and second spring means guided by said rod and poised for compressional reaction between said first body part and said offset end portion.

9. Apparatus according to claim 8, in which the fixation of each of said rods to said first body part is such as to compressionally preload both said spring means on each of said spaced parallel longitudinal axes.

10. Apparatus according to claim 9, in which the respective spring means on each of said rods comprises a stacked plurality of dished-washer spring elements.

11. Apparatus according to claim 5, in which said third body part integrally includes a transversely offset end portion that is in radial overlap with the end of said first body part remote from the headed end of said first body part, said rod-and-bore engagement being via said transversely offset end portion.

12. Apparatus according to claim 11, in which said rod-and-bore engagement comprises a bolt that is headed at one end and has a cylindrical shank which is guided in a bore in said transversely offset end portion and which has threaded engagement to a tapped bore in said first body part; said resilient snubber means comprising a first snubber carried by said shank and interposed between said transversely offset end portion and the adjacent end of said first body part, and a second snubber carried by said shank and interposed between the headed end of said bolt and said transversely offset end portion.

13. Apparatus according to claim 12, in which the threaded engagement of said bolt to said tapped bore compressionally and axially preloads both snubbers.

14. Apparatus according to claim 13, in which said rod-and-bore engagement comprises aligned bores in said offset end portion and in said first body part, a rod supported in and fixed to said first body part and projecting through the bore of said offset end portion, said rod having a headed outer end, first spring means guided by said rod and poised for compressional reaction between said headed outer end and said offset end portion, and second spring means guided by said rod and poised for compressional reaction between said first body part and said offset end portion.

15. Apparatus according to claim 14, in which the fixation of said rod to said first body part is such as to compressionally preload both said spring means.

16. Apparatus according to claim 14, in which each of said spring means comprises a stacked plurality of dished-washer spring elements.

17. Apparatus according to claim 12, in which the other end of said third body part is at longitudinal offset from the headed end of said first body part, and a single transversely oriented link connection between said other end of the third body part and said first body part, said link connection being via spaced parallel pins which define a geometric plane that is substantially normal to said longitudinal axis.

18. Orthopedic bone-fixator apparatus, for the dynamic repair of a bone fracture, comprising an elongate extendable generally cylindrical body about a longitudinal axis that is common to a cylindrical head at each of the opposite ends of said body, said body comprising:
first and second body parts having longitudinally lapped elongate generally semicylindrical portions each of which is integrally formed with one to the exclusion of the other of said heads;
each of said heads being adapted for selectively locked ball-joint connection of a bone-pin mount to each of the respective first and second body parts;
a third elongate body parts carried by the generally semi-cylindrical portion of said first body part, said third part having a cross-sectional guidance contour that is constant over the longitudinal extent thereof;
said second body part having an internal elongate cavity of constant cross-section having longitudinally guided conformance to and coaction with the constant cross-sectional guidance contour of said third body part, and a releasable clamp coacting between said second and third body parts for selectively determining a fixed longitudinal position of second body-part connection to said third body part; and means including at least one longitudinal rod-and-bore engagement and resilient snubber means establishing limited resiliently snubbed and longitudinally guided displaceability of said third body part with respect to said first body part.

19. Apparatus according to claim 18, in which one end of said third body part is in confronting relation with and at longitudinal offset from the headed end of said first body part, and a single transversely oriented link connection between one end of the third body part and said first body part, said link connection being via spaced parallel pins which define a geometric plane that is substantially normal to said longitudinal axis.

20. Apparatus according to claim 19, wherein each of said spaced parallel pins is elastomerically bushed in its link and body-part connections.

21. Orthopedic bone-fixator apparatus, for the dynamic repair of a bone fracture, comprising an elongate body having a longitudinal axis that is common to a head at each of the opposite ends of said body, said body comprising:

first and second body parts having longitudinally lapped portions each of which has an outer end which is integrally formed with one to the exclusion of the other of said heads;

each of said heads being adapted for selectively locked ball-joint connection of a bone-pin mount to each of the respective first and second body parts;

a third elongate body part carried by the lapped portion of said first body part;

first longitudinal guide means and a releasable clamp coacting between said second and third body parts for selectively determining a fixed longitudinal position of second body-part connection to said third body part;

second longitudinal guide means coacting between said first body part and one longitudinal end of said third body part;

third longitudinal guide means coacting between said first body part and the opposite longitudinal end of said third body part; and resilient snubber means coacting between said first and third body part for providing resiliently snubbed opposition to relative displacement of said first and third body parts.

22. Apparatus according to claim 21, in which each of said second and third longitudinal guide means includes at least one longitudinal rod-and-bore engagement.

* * * * *